US00PP34276P2

(12) United States Plant Patent
Kolster et al.

(10) Patent No.: US PP34,276 P2
(45) Date of Patent: May 31, 2022

(54) ***HYDRANGEA* PLANT NAMED 'HOKOMABAVI'**

(50) Latin Name: *Hydrangea macrophylla*
Varietal Denomination: Hokomabavi

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: Horteve Breeding BV, Aalsmeer (NL), Part Interest; Kolster Holding BV, Boskoop (NL), Part Interest ( * ) Notice: Subject to any disclaimer, the term of this patent is extended or adjusted under 35 U.S.C. 154(b) by 0 days.

(21) Appl. No.: 17/505,485

(22) Filed: Oct. 19, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea macrophylla* plant named 'Hokomabavi' that is characterized by its sterile flowers with strongly undulate sepals, its sterile flowers with strongly undulate sepals, its compact plant habit, its inflorescences sterile flower sepals that are dark pink in color, and its suitability for growing in containers.

2 Drawing Sheets

Botanical classification: *Hydrangea macrophylla.*
Varietal denomination: 'Hokomabavi'.

BACKGROUND OF THE INVENTION

The present invention relates to a new and distinct cultivar of *Hydrangea macrophylla* and will be referred to hereafter by its cultivar name, 'Hokomabavi'. 'Hokomabavi' represents a new mophead type *Hydrangea*, a deciduous shrub grown for use as a landscape plant.

'Hokomabavi' was derived from an ongoing breeding program conducted by the Inventors in Boskoop, The Netherlands. The objectives of the breeding program are to develop new cultivars of *Hydrangea macrophylla* with strongly undulate sterile flower sepals.

The Inventors made a controlled cross in October of 2012 in Boskoop, The Netherlands between unnamed and unpatented proprietary plants from their breeding program; female parent (ref. code 09-025-10) and male parent (ref. code 10-001-02). 'Hokomabavi' was selected in June of 2014 as a single unique plant amongst the resulting seedlings.

Asexual propagation of the new cultivar was first accomplished under the direction of the Inventors by stem cuttings in August of 2014 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomabavi' as a unique cultivar of *Hydrangea.*

1. 'Hokomabavi' exhibits sterile flowers with strongly undulate sepals.
2. 'Hokomabavi' exhibits a compact plant habit.
3. 'Hokomabavi' exhibits inflorescences sterile flower sepals that are dark pink in color.
4. 'Hokomabavi' exhibits suitability for growing in containers.

The female parent of 'Hokomabavi' differs from 'Hokomabavi' in having sterile flower sepals that are lighter pink in color and less undulate. The male parent of 'Hokomabavi' differs from 'Hokomabavi' in having sterile flower sepals with margins that are white in color and are slightly serrated. 'Hokomabavi' can be most closely compared to the *Hydrangea macrophylla* cultivars 'Surfing Safari Seaside' (not patented) and 'Surfing Safari White Waves' (not patented). Both 'Surfing Safari Seaside' and 'Surfing Safari White Waves' are similar to 'Hokomabavi' in having sterile flowers with sepals that are strongly undulate and in being suitable for growing in containers. 'Surfing Safari Seaside' differs from 'Hokomabavi' in having sterile flower sepals that are light pink in color. 'Surfing Safari White Waves' differs from 'Hokomabavi' in having sterile flower sepals that are white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Floraldaily and Growertalks.

BRIEF DESCRIPTION OF THE DRAWINGS

The accompanying color photographs illustrates the overall appearance and distinct characteristics of the new *Hydrangea*. The photographs were taken of a 2-year-old plant as grown in a greenhouse in a 19-cm container in Boskoop, The Netherlands.

The photograph in FIG. 1 provides a side view of the plant habit of 'Hokomabavi' in bloom.

Figure 1:
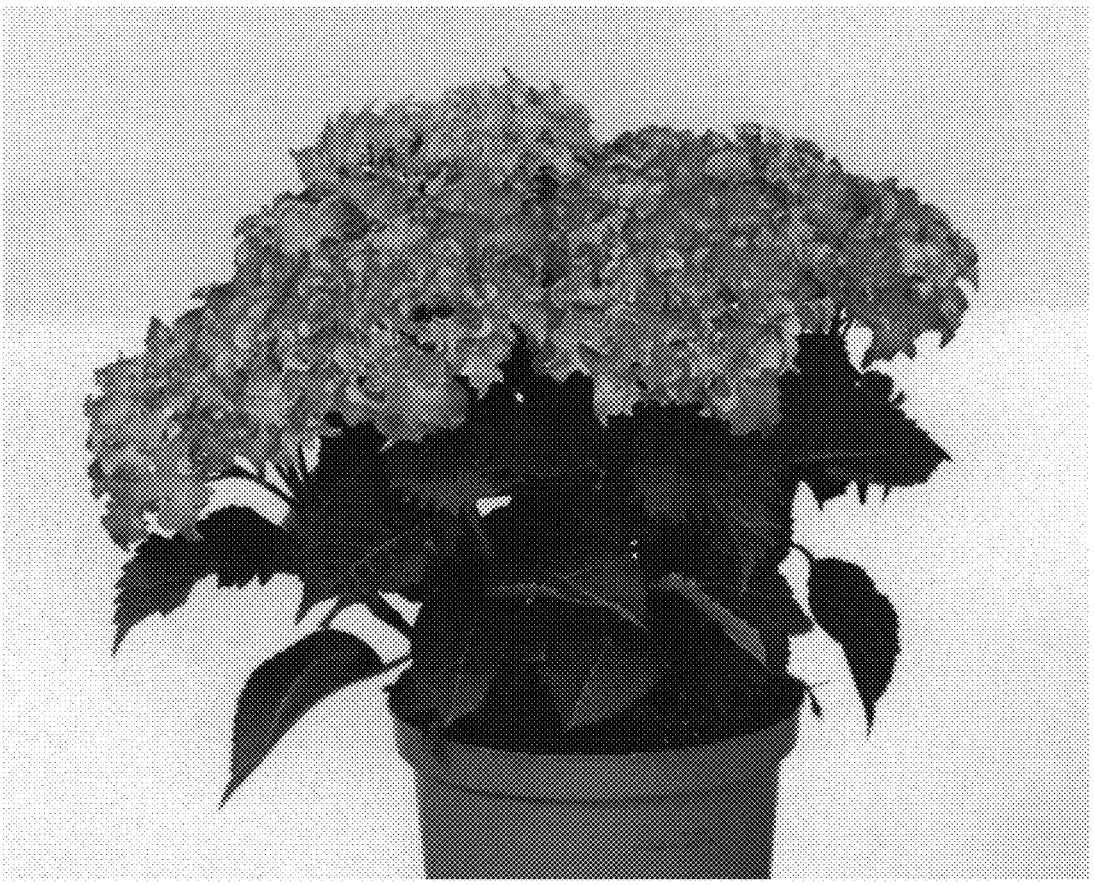
Figure 2:
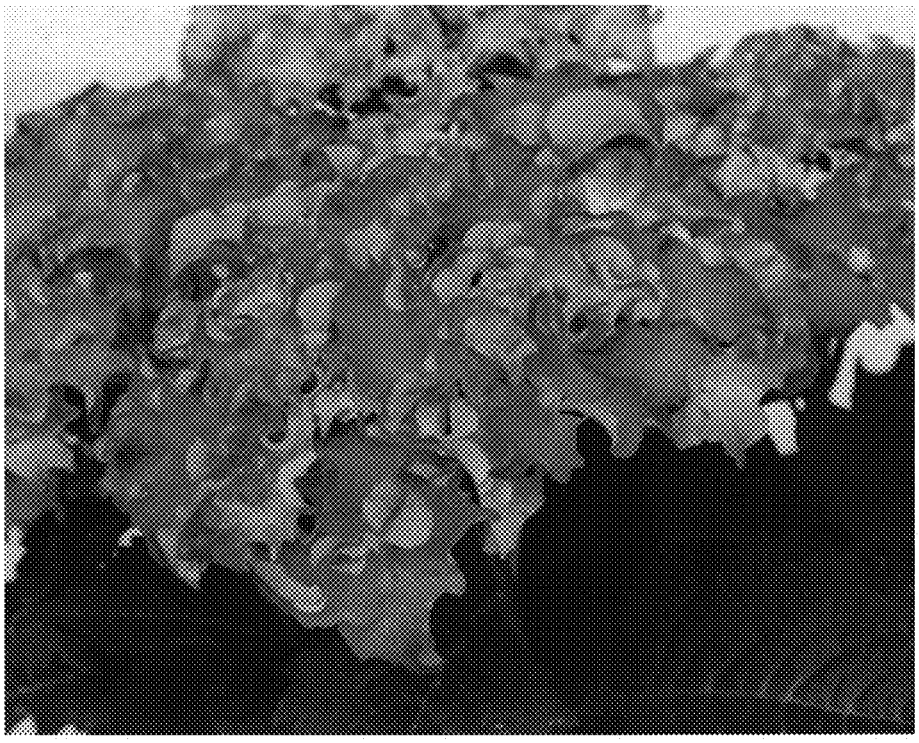

The photograph in FIG. 2 provides a close-up view of the inflorescences of 'Hokomabavi'.

Figure 3:
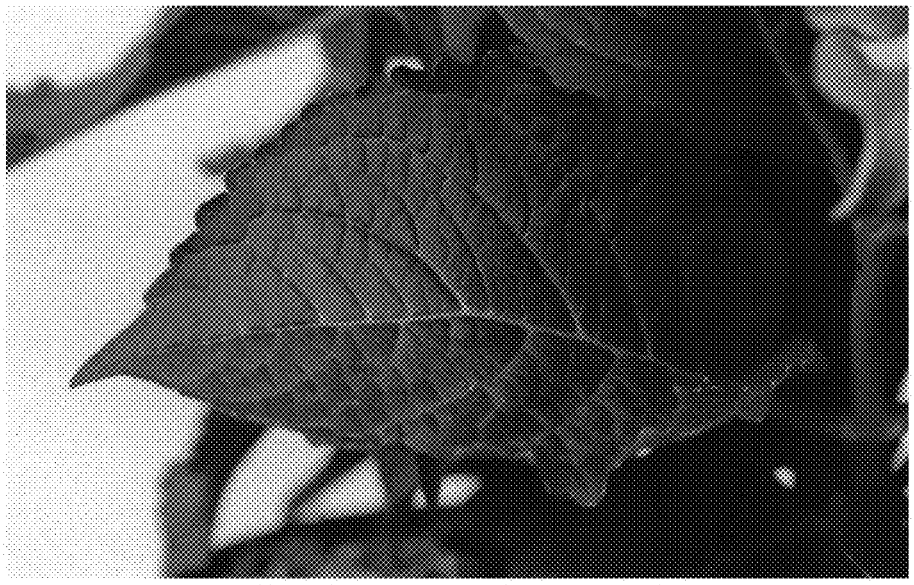

The photograph in FIG. 3 provides a close-up view of a leaf of 'Hokomabavi'.

The colors in the photographs may differ slightly from the color values cited in the detailed botanical description, which accurately describe the colors of the new *Hydrangea*.

BOTANICAL DESCRIPTION OF THE PLANT

The following is a detailed description of 2-year-old plants of 'Hokomabavi' as grown in a greenhouse in a 19-cm container in Boskoop, The Netherlands. The phenotype of the new cultivar may vary with variations in environmental, climatic, and cultural conditions, as it has not been tested under all possible environmental conditions. The plants were grown under non-blueing conditions and blueing conditions have not been tested. The color determination is in accordance with The 2015 Colour Chart of The Royal Horticultural Society, London, England, except where general color terms of ordinary dictionary significance are used.

General description:

*Blooming period*.—Late spring to late summer in The Netherlands, retaining color for at least 2 months.

*Plant type*.—Deciduous shrub, mophead type *Hydrangea*.

*Plant habit*.—Compact, suitable for container growing.

*Height and spread*.—Average of 35.3 cm in height and 45.3 cm in spread as an 18-month-old plant and 1 m in height and spread when grown in the landscape.

*Hardiness*.—At least to U.S.D.A. Zones 5 to 9.

*Diseases and pests*.—No resistance or susceptibility to diseases or pests has been observed.

*Root description*.—Fine and fibrous, NN155B in color.

*Propagation*.—Softwood stem cuttings.

*Growth rate*.—Moderate.

*Root development*.—Time required for root initiation is 6 weeks, time required to produce a young plant from rooted cutting is 18 weeks.

Stem description:

*Stem shape*.—Rounded.

*Stem strength*.—Strong.

*Stem color*.—Young; 143C, mature; a blend of 143B and 144A, slightly tinged 183C at the nodes, older bark; ranging between 199B to 199C and 200A to 200B.

*Stem size*.—Lateral branch an average of 14.1 cm in length, 6 mm in diameter.

*Stem surface*.—Younger and mature stems; glabrous and slightly glossy, lenticellate, lenticles; an average of 1 mm in length and 0.75 mm in width, a blend of N186C and 200A in color, old growth at base; bark-like, mostly smooth and can be slightly exfoliating.

*Internode length*.—Average of 3.8 cm.

*Branching*.—Moderately to freely branching, held in an average angle of 55° to horizontal, an average of 7 lateral branches per main branch.

*Stipules*.—Persistent, 2 opposite at base of petioles, stipule bud; is 1.5 mm in length, 0.5 mm in width, 187A in color, oblong in shape, acute apex, matte surface.

Foliage description:

*Leaf shape*.—Broadly ovate.

*Leaf arrangement*.—Opposite.

*Leaf division*.—Simple.

*Leaf base*.—Attenuate to obtuse.

*Leaf apex*.—Short apiculate.

*Leaf margins*.—Coarsely crenate-serrate.

*Leaf venation*.—Pinnate, upper side 144A, lower side 145A to 145B.

*Leaf size*.—Average of 12.3 cm in length and 8.7 cm in width.

*Leaf attachment*.—Petiolate.

*Leaf surface*.—Both surfaces smooth and very slightly rugose.

*Leaf color*.—Young upper surface; 137B, young lower surface; 138B, mature upper surface; a blend of NN137A and N189A, mature lower surface; 137B.

*Petioles*.—An average of 2.2 cm in length, 4 mm in width, both surfaces glabrous and slightly glossy, upper surface color; 145A, margins 144A, lower surface color; 144A.

Inflorescence description:

*Inflorescence type*.—Terminal panicle, full rounded mophead in form, comprised of single sterile flowers and inconspicuous fertile flowers, flattened globular in shape.

*Lastingness of inflorescence*.—Persistent at least 2 months in color.

*Inflorescence number*.—One per lateral.

*Inflorescence size*.—Average of 12.1 cm in height, 17.9 cm in diameter.

*Flower number*.—Average of 65 sterile flowers and 35 fertile flowers per panicle.

*Flower fragrance*.—None.

*Flower aspect*.—Upright to outward.

*Flower size*.—Sterile flowers; an average of 5.2 cm in diameter, 1.8 cm in depth, fertile flowers; an average of 1.1 cm in diameter and 6.5 mm in depth.

*Flower type*.—Rotate.

*Flower buds*.—Sterile flowers; average of 8 mm in length, 1.6 cm in diameter, broadly irregular cup-shaped, margins of immature sepals strongly undulate, color; 144C and N144D, base 145B, fertile flowers; average of 6 mm in length and 4.5 mm in diameter, broadly obovate in shape, color; 58D, tip 61D, immature ovary 145A to 145B.

*Peduncles*.—Strong, held in an average angle of 25° to main peduncle, average of 5.2 cm in length and 3.7 mm in width, color; 145A, top 148D, tinged 178A to 178B at the nodes and lenticels, surface is moderately to densely covered with very short soft hairs, average of 0.3 mm in length, matches surface color.

*Pedicels*.—Moderately strong, average of 3.2 mm in length and 2 mm in width, held in an average angle of 25° , color; young and mature pedicels 65A, flushed with 53D, and moderately covered with very fine woolly hairs that match surface color and 0.3 mm in length.

*Petals*.—Sterile flowers; 5, occasionally 4, rotate, 4 mm in length, 2.5 mm in diameter, ovate, concave in shape, acute apex, cuneate base, entire margins, cup-shaped, glabrous and matte surface, colors; when opening and fully open upper surface N66C, margins 76D, when opening and fully open lower surface 68B, fertile flowers; 5, rotate, 5 mm in length, 3 mm in width, ovate, concave in shape, acute apex, cuneate base, entire margins, cup-shaped, glabrous and matte surface, color; when opening and fully open upper surface; N66C, margins 76D, when fully open upper and lower surface; 68C.

*Sepals*.—Sterile flowers; showy, 4 to occasionally 5, reniform to broadly deltoid and slightly concave in shape, moderately to strongly overlapping, rotate in arrangement, entire margins strongly undulate, apex is bluntly acute, broad attenuate base, average of 3 cm in length and width, upper and lower surface glabrous and matte, color: when opening upper surface; 68C, top 58B to 58C, when opening lower surface; 62C, marbles and tinged 150D, when fully open upper surface; 63A, strongly flushed and tinged at the top with a blend of 144A and 178A to 178B, fading to a blend of 178A to 178B, when fully open lower surface; 63C, strongly flushed and tinged at the top with 145A, fading to a blend of 145A to 146B to 146D, fertile flowers; 5, rotate in arrangement, deltoid in shape, entire margins, broadly acute apex, broadly cuneate base, average of 1.75 mm in length and 1.5 mm in width, both surfaces are glabrous and matte, color; when opening and fully open upper surface; 63C, base 150D, fading to a blend of 63B to 63C, when opening and fully open lower surface; 150D, top 182B to 182D, fading to a blend of 182B to 182C.

Reproductive organs:

*Stamens*.—Sterile flowers; average of 8, anther is broad oblong in shape, 0.75 mm in diameter, 155D in color, filament is 2 mm in length, N155D in color, pollen is low in quantity and 155C in color, fertile flowers; average of 10, anther is broad oblong in shape, 0.5 mm in length, 155D in color, filament is 5 mm in length and NN155D in color, pollen is low in quantity and 155C in color.

*Pistils*.—Sterile flowers; average of 3, occasionally 2, an average of 1.5 mm in length, stigma is club-shaped, 1 mm in diameter and NN155A in color, style is 155D in color, ovary is 1 mm in diameter, NN155D in color and inferior, fertile flowers; average of 3, an average of 2 mm in length, stigma is cub-shaped and NN155A in color, style is 1.5 mm in length, 155D in color, ovary is 1 mm in diameter, 150D in color and inferior.

*Fruit and seed*.—None observed to date.

It is claimed:

1. A new and distinct cultivar of *Hydrangea* plant named 'Hokomabavi' substantially as herein illustrated and described.

* * * * *